United States Patent
Ito et al.

(10) Patent No.: US 9,285,582 B2
(45) Date of Patent: Mar. 15, 2016

(54) OPTICAL SCANNING ENDOSCOPE

(71) Applicant: HOYA CORPORATION, Tokyo (JP)

(72) Inventors: Shunichi Ito, Tokyo (JP); Masao Takahashi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/378,733

(22) PCT Filed: Feb. 20, 2013

(86) PCT No.: PCT/JP2013/054145
§ 371 (c)(1),
(2) Date: Aug. 14, 2014

(87) PCT Pub. No.: WO2013/129204
PCT Pub. Date: Sep. 6, 2013

(65) Prior Publication Data
US 2015/0029570 A1    Jan. 29, 2015

(30) Foreign Application Priority Data

Mar. 2, 2012 (JP) .................................. 2012-046172

(51) Int. Cl.
G02B 26/10 (2006.01)
G02B 23/26 (2006.01)
A61B 1/00 (2006.01)
G02B 23/24 (2006.01)

(52) U.S. Cl.
CPC .......... G02B 26/103 (2013.01); A61B 1/00172 (2013.01); G02B 23/24 (2013.01); G02B 23/2476 (2013.01); G02B 23/26 (2013.01)

(58) Field of Classification Search
CPC .. G02B 26/103; G02B 23/26; G02B 23/2476; G02B 23/24; A61B 1/00172
USPC .......... 359/198.1, 199.4, 200.8, 209.1, 211.2; 385/116–118; 600/160, 175, 182
See application file for complete search history.

(56) References Cited

U.S. PATENT DOCUMENTS 6,294,775 B1    9/2001    Seibel et al.
8,226,551 B2    7/2012    Sugimoto
(Continued)

FOREIGN PATENT DOCUMENTS

JP    2001-170002    6/2001
JP    2010-162089    7/2010
(Continued)

Primary Examiner — Frank Font
(74) Attorney, Agent, or Firm — Greenblum & Bernstein P.L.C.

(57) ABSTRACT

An optical scanning endoscope with an optical fiber, and a fiber driving unit with a plurality of actuators which bend side surfaces of the optical fiber by applying a pressing force. A mounting member is a substantially cylindrical molded interconnect device (MID) component which supports the fiber driving unit. A control circuit supplies driving signals to each of the actuators to control the bending amount and direction of the optical fiber. A wiring member electrically connects wiring patterns on the mounting member with the control circuit. The mounting member has a planar surface section at one proximal-end-surface side of the cylindrical outer-peripheral surface. The wiring patterns include at least first patterns having one end portion disposed on the planar surface section to form soldering lands. The other end portions are electrically connected to the actuators on the proximal-end surface of the mounting member. The wiring member is connected to the soldering lands.

12 Claims, 10 Drawing Sheets

(56) References Cited

U.S. PATENT DOCUMENTS

| | | |
|---|---|---|
| 8,258,457 B2 | 9/2012 | Kobayashi |
| 8,348,836 B2 | 1/2013 | Sugimoto |
| 8,466,956 B2 | 6/2013 | Sugimoto et al. |
| 2004/0176661 A1* | 9/2004 | Futatsugi ................. 600/110 |
| 2006/0058584 A1* | 3/2006 | Hirata ..................... 600/179 |
| 2008/0177144 A1* | 7/2008 | Otawara .................. 600/157 |
| 2008/0265178 A1 | 10/2008 | Johnston |
| 2009/0026888 A1 | 1/2009 | Melville |

FOREIGN PATENT DOCUMENTS

| | | |
|---|---|---|
| JP | 2010-527028 | 8/2010 |
| JP | 2010-534862 | 11/2010 |
| JP | 2011-30720 | 2/2011 |
| JP | 2011-104239 | 6/2011 |
| JP | 2011-115252 | 6/2011 |
| JP | 2011-217836 | 11/2011 |

* cited by examiner

OPTICAL SCANNING ENDOSCOPE

TECHNICAL FIELD

The present invention is related to an optical scanning endoscope, which scans an observation portion optically by light guided through an optical fiber and receives the light reflected on the observation portion to form an image. More specifically, the present invention is related to an optical scanning endoscope with a fiber driving unit mounted on the optical scanning endoscope, which is configured with an MID (Molded Interconnect Device) component.

BACKGROUND ART

In recent years, an optical scanning endoscope, which scans an observation portion optically in a spiral form by light guided through an optical fiber and receives the light reflected on the observation portion to form an image, is suggested (e.g., U.S. Pat. No. 6,294,775 and Japanese Patent Provisional Publication No. 2010-162089). The optical scanning endoscope is equipped with a single-mode optical fiber in an endoscope therein, which is held in a state of a cantilever by a piezoelectric actuator arranged in the vicinity of a tip end of the optical fiber. The piezoelectric actuator vibrates (resonates) the tip end of the optical fiber two-dimensionally in accordance with a characteristic frequency while modulating and amplifying the amplitude of the vibration so that the tip end of the optical fiber is driven in the spiral form. As a result, illumination light guided from a light source through the optical fiber is emitted to scan on the observation portion in the spiral form, and an image corresponding to an illuminated range (a scanning area) is obtained.

SUMMARY OF THE INVENTION

A configuration of a tip end of an optical fiber in a conventional optical scanning endoscope will be described with reference to FIG. 12. As shown in FIG. 12, in the vicinity of the tip end of an optical fiber 2, arranged is a fiber driving unit 23, which is supported by a mounting member 22 and fixed to an insertion tube (not shown) in the optical scanning endoscope. The fiber driving unit 23 has a cylindrical shape and has the optical fiber 2 inserted along a cylinder axis thereof. On an outer periphery of the cylindrical surface of the fiber driving unit 23, four (4) piezoelectric actuators are provided at each 90 degrees, and the tip end of the optical fiber 2 is configured to bend by feeding driving signals to electrodes 23X, 23X', 23Y, 23Y' provided on the surface of the piezoelectric actuators.

In order to feed the driving signals to the actuators in the fiber driving unit 23, it is necessary that the electrodes 23X, 23X', 23Y, 23Y' of the piezoelectric actuators are connected with an unshown driving circuit; therefore, lead wires 12 are soldered onto surfaces of the electrodes 23X, 23X', 23Y, 23Y' of the piezoelectric actuators. However, while an outer diameter of the fiber driving unit 23 is notably small (e.g., $\phi 0.8$ mm), an operation to solder the lead wires 12 on the outer periphery of the cylindrical surface at each 90 degrees is difficult to be automated, and when the soldering is operated manually, operation efficiency (i.e., yield rate) is particularly lowered.

Further, due to the manual soldering operation, it is necessary to consider reserving soldering margins and extra lengths (bulges) along a longitudinal direction of the optical fiber 202A, which require redundant space in the vicinity of the tip end of the optical fiber 202A.

The present invention is made in view of the above described circumstances. That is, the object of the present invention is to downsize the diameter of the tip end portion of the optical fiber in the optical scanning endoscope and improve the yield rate in manufacturing the optical scanning endoscope.

In order to achieve the above described object, an optical scanning endoscope according to the present invention is provided with an optical fiber configured to guide light entering from an incident end thereof to an emitting end thereof and to emit the light from the emitting end; a fiber driving unit arranged in vicinity of the emitting end of the optical fiber and including a plurality of actuators, the plurality of actuators being configured to bend the optical fiber by pressing laterals of the optical fiber in directions orthogonal to a longitudinal direction of the optical fiber; a mounting member being a substantially cylindrically-formed MID (Molded Interconnect Device) component with a surface, on which a plurality of wiring patterns are formed, the mounting member supporting the fiber driving unit along a cylinder axis; a control circuit configured to feed driving signals to each of the plurality of actuators and control an amount of bending and a direction of bending of the optical fiber; and a wiring member configured to electrically connect the plurality of wiring patterns of the mounting member with the control circuit. The mounting member includes a plane section at a part on an outer periphery of a cylindrical surface of the mounting member on a proximal-end face side of the mounting member. The plurality of wiring patterns are arranged such that end portions thereof on one side are placed on the plane section to form a plurality of soldering lands thereat, the plurality of wiring patterns including at least a plurality of first patterns, each end portion of which on the other side is electrically connected with one of the plurality of actuators respectively on the proximal-end face of the mounting member. The wiring member is connected to the plurality of soldering lands.

According to this configuration, connection of the wiring member with a plurality of actuators electrically can be accomplished on the plane section of the mounting member; therefore, efficiency in an assembling operation can be improved.

Optionally, it may be preferable that each of the plurality of soldering lands is arranged on the plane section to be spaced apart from each other at a predetermined interval along the direction orthogonal to the longitudinal direction of the optical fiber. According to this configuration, the wiring member can be arranged to align along the direction orthogonal to the longitudinal direction of the optical fiber; therefore, the efficiency in the assembling operation can be even more improved.

Optionally, the plurality of wiring patterns may include a plurality of second patterns, end portions of which on the other side are connected to a functional component on a tip-end face of the mounting member. According to this configuration, even if the functional component is added in the vicinity of the emitting end of the optical fiber, it may not be necessary to prepare a new wiring path.

Optionally, the soldering lands of the plurality of first patterns may be arranged on a proximal-end face side of the plane section, and the soldering lands of the plurality of second patterns may be arranged on a tip-end face side of the plane section. Further, in this regard, it may be preferable that the soldering lands of the plurality of first patterns and the soldering lands of the plurality of second patterns are arranged not to face one another on the plane section. According to this configuration, when the wiring member is connected to the soldering lands, adjoining wiring members may be prevented from being interfered with one another; therefore, the efficiency in the assembling operation can be even more improved.

Optionally, the plane section may include a plurality of stepwise planes which are formed to be lower in heights thereof from the tip-end face side toward the proximal-end face side; the soldering lands of the plurality of first patterns may be arranged on one of the plurality of stepwise planes which is closest to the proximal-end face; and the soldering lands of the plurality of second wiring patterns may be arranged on a different one of the plurality of stepwise planes from the soldering lands of the first wiring patterns. According to this configuration, arrangement of the wiring member may be divided into the plurality of steps on the mounting member; therefore, interference among adjoining wiring members may be reduced, and the efficiency in the assembling operation can be even more improved.

Optionally, it may be preferable that the functional component is a thermistor.

Optionally, it may be preferable that the wiring member is lead wires.

Optionally, it may be preferable that the wiring member is a flexible board.

According to the configuration of the present invention, wiring connection of the fiber driving unit of the optical scanning endoscope can be conducted on the plane section formed on the mounting member; therefore, efficiency of the soldering operation can be significantly improved. Further, it is not necessary to take extra length (a curve) for the wiring and the like into consideration, but the wiring can be arranged substantially linearly; therefore, the tip end portion of the optical fiber in the optical scanning endoscope may be downsized in the diameter thereof.

EMBODIMENTS FOR CARRYING OUT THE INVENTION

Hereinafter, embodiments of the present invention will be described with reference to the accompanying drawings.

Figure 1:
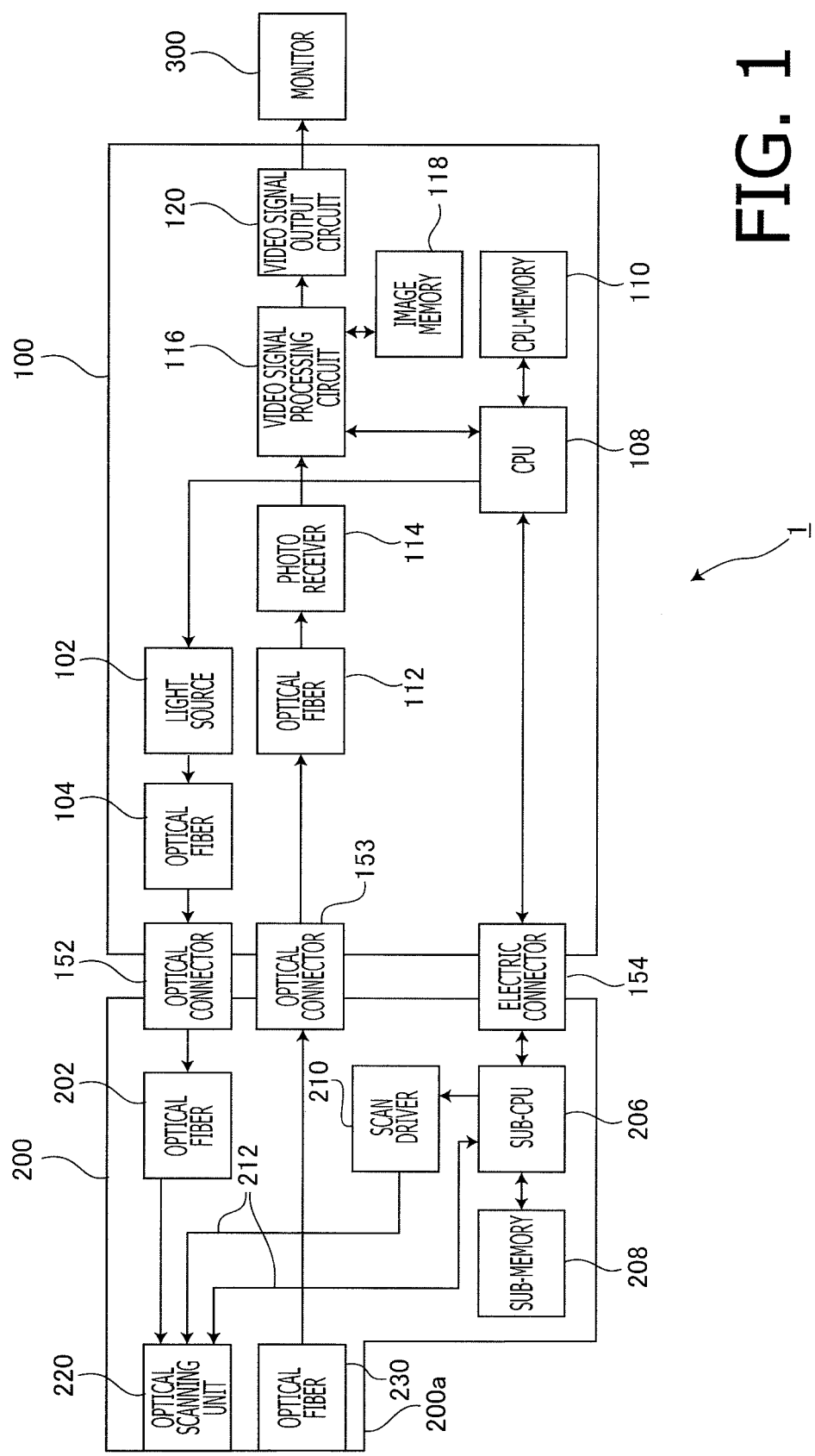
FIG. 1 A block diagram to illustrate a configuration of an optical scanning endoscope apparatus having an optical scanning endoscope according to a first embodiment of the present invention.

FIG. 1 is a block diagram to illustrate a configuration of an optical scanning endoscope apparatus having an optical scanning endoscope according to a first embodiment of the present invention. The optical scanning endoscope apparatus 1 is configured with a processor (general-side block) 100, an optical scanning endoscope (patient-side block) 200, and a monitor 300.

The processor 100 includes a light source 102, an optical fiber 104, a CPU 108, a CPU memory 110, an optical fiber 112, a photo receiver 114, a video signal processing circuit 116, an image memory 118, and a video signal output circuit 120. The optical scanning endoscope 200 includes an optical fiber 202, an optical scanning unit 220, an optical fiber 230, a sub-CPU 206, a sub-memory 208, and a scan driver 210.

The light source 102 includes a red-light laser (not shown) to emit red light, a green-light laser (not shown) to emit green light, and a blue-light laser (not shown) to emit blue light. The light source 102 combines the laser in these colors to generate and emit white light (hereinafter, "illumination light"). The illumination light enters a proximal-end portion of the optical fiber 104. A tip end portion of the optical fiber 104 is coupled to an optical connector 152, which optically connects the processor 100 with the optical scanning endoscope apparatus 200. Thus, the illumination light entering the proximal-end portion of the optical fiber 104 passes through the optical connector 152 and enters an optical system disposed inside the optical scanning endoscope 200.

The proximal-end portion of the optical fiber 202 is optically coupled to the optical fiber 104 through the optical connector 152. The tip end portion of the optical fiber 202 is accommodated in the optical scanning unit 220, which is installed in a tip end portion of an insertion tube 200a of the optical scanning endoscope 200. Thus, the illumination light exiting the optical fiber 104 passes through the optical connector 152, enters the proximal-end portion of the optical fiber 202, travels through the optical fiber 202, and is thereafter emitted from the tip end of the optical fiber 202.

Figure 2:
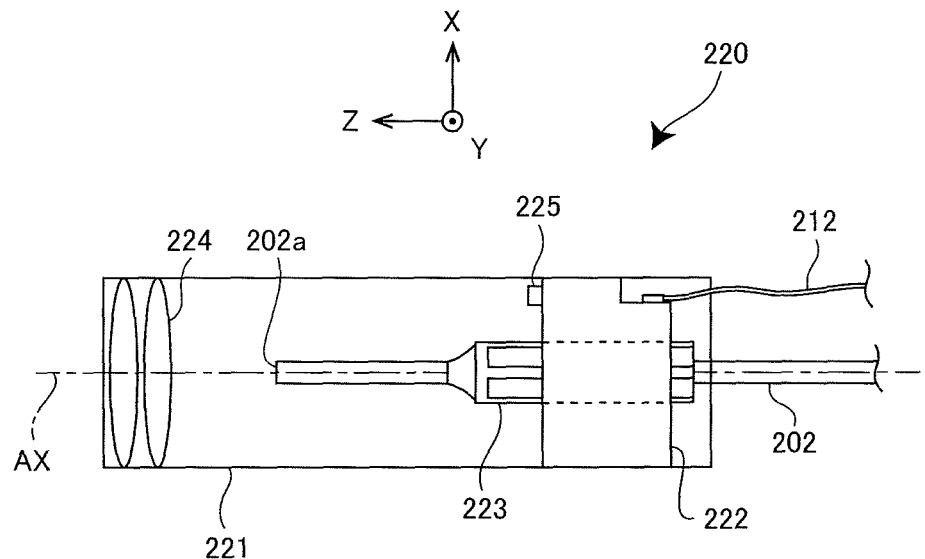
FIG. 2 An overall diagram to illustrate a configuration of an optical scanning unit installed in the optical scanning endoscope according to the first embodiment of the present invention.

FIG. 2 is an overall diagram to illustrate a configuration of the optical scanning unit 220. In the following description, for the purpose of illustrating the optical scanning unit 220, a longitudinal direction of the optical scanning unit 220 is defined as a Z-direction, and two directions which are orthogonal to the Z-direction and orthogonal to each other are defined as an X-direction and a Y-direction. As shown in FIG. 2, the optical scanning unit 220 includes a metal-made hollow tube 221, which accommodates various components. The hollow tube 221 is arranged in an orientation to be in axially parallel with an axial direction of the insertion tube 200a of the optical scanning endoscope 200 and is fixed to a tip end portion of the insertion tube 200a. The optical fiber 202 is accommodated and supported inside the hollow tube 221 by a biaxial actuator 223 (fiber driving unit) and the mounting member 222, and functions as a two-dimensional point light source of the optical scanning endoscope 200. A position of a tip end 202a providing the point light source changes periodically under control of the CPU 108.

The sub-memory 208 (FIG. 1) stores probe information, such as identifying information and various properties of the optical scanning endoscope 200. The sub-CPU 206 reads out the probe information from the sub-memory 208 upon starting up of the system and transmits the information to the CPU 108 through an electric connector 154, which connects the processor 100 with the optical scanning endoscope 200 electrically. The CPU 108 stores the transmitted probe information in the CPU memory 110. The CPU 108 reads out the stored probe information when necessary, generates signals which are needed to control the optical scanning endoscope 200, and transmits the signals to the sub-CPU 206. The sub-CPU 206 designates setting values required for the scan driver 210 in accordance with the control signals transmitted from the CPU 108.

Figure 3:
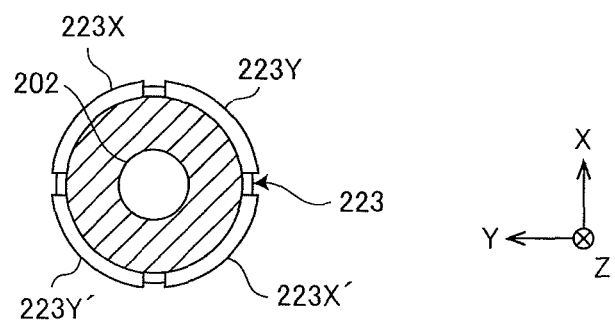
FIG. 3 A cross-sectional view to illustrate an overall configuration of a biaxial actuator installed in the optical scanning endoscope according to the first embodiment of the present invention.

The scan driver 210 generates drive signals corresponding to the designated setting values and drives the cylindrical-shaped biaxial actuator 223, which is adhesively fixed to the outer peripheral surface of the optical fiber 202 in the vicinity of the tip end 202a. FIG. 3 is a cross-sectional view to illustrate an overall configuration of the biaxial actuator 223. As shown in FIG. 3, the biaxial actuator 223 is a piezoelectric actuator, in which a pair of X-axis electrodes ("223X" and "223X'" in the figure) and Y-axis electrodes ("223Y" and "223Y'" in the figure) centered about the optical fiber 202 are provided on a piezoelectric body, and the electrodes form four independent actuators, respectively. According to the present embodiment, the drive signals from the scan driver 210 are fed to the electrodes 223X, 223X', 223Y, 223Y' in the piezoelectric actuators through a lead wire 212 (FIG. 2), which connects the scan driver 210 with the mounting member 222, and wiring patterns P1-P4, which are formed on the mounting member 222 (details will be described later).

Figure 4:
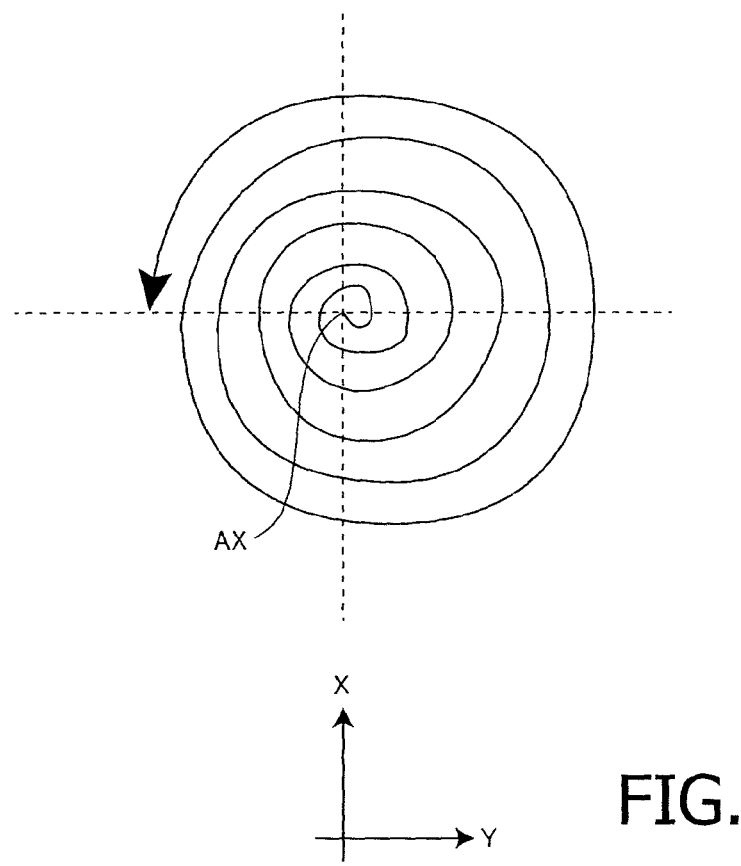
FIG. 4 A diagram to illustrate a rotation trajectory of a tip end of the optical fiber.

The scan driver 210 applies an alternating voltage X (drive signals) between the X-axis electrodes 223X and 223X' in the biaxial actuator 223 so that the piezoelectric body is resonated in the X-direction. Further, the scan driver 210 applies an alternating voltage Y (drive signals), of which frequency is the same as that of the alternating voltage X and of which phase is orthogonal to the alternating voltage X, between the Y-axis electrodes 223Y and 223Y' in the biaxial actuator 223 so that the piezoelectric body is resonated in the Y-direction. The alternating voltages X, Y are defined as voltages, which linearly increase in amplitudes in proportion to time and reach effective values (X), (Y) by taking times (X) and (Y), respectively. The tip end 202a of the optical fiber 202 rotates to draw a spiral pattern centered at a center axis AX on a plane (hereinafter, an "XY approximate plane"), which approximates an X-Y plane, due to combination of kinetic energies by the biaxial actuator 223 in the X-direction and the Y-direction. A rotation trajectory of the tip end 202a becomes larger in proportion to the voltages applied and reaches to draw a circle having a maximum diameter when the alternating voltages of the effective values (X), (Y) are applied. FIG. 4 illustrates the rotation trajectory of the tip end 202a on the XY approximate plane. While the rotation trajectory of the tip end 202a tends to vary depending on an ambient temperature around the biaxial actuator 223 (i.e., the rotation trajectory has a temperature characteristic), in the present embodiment, the optical scanning endoscope 200 is equipped with a heater (not shown) inside the hollow tube 221 so that the temperature is monitored through a thermistor 225 (FIG. 2) disposed on a tip-end face of the mounting member 222, and the temperature around the biaxial actuator 223 is controlled to be constant (e.g., 42 degrees C.). As will be described later, the thermistor 225 is connected to the sub-CPU 206 through the lead wire 212, and the temperature thereof is controlled by the sub-CPU 206.

Figure 5:
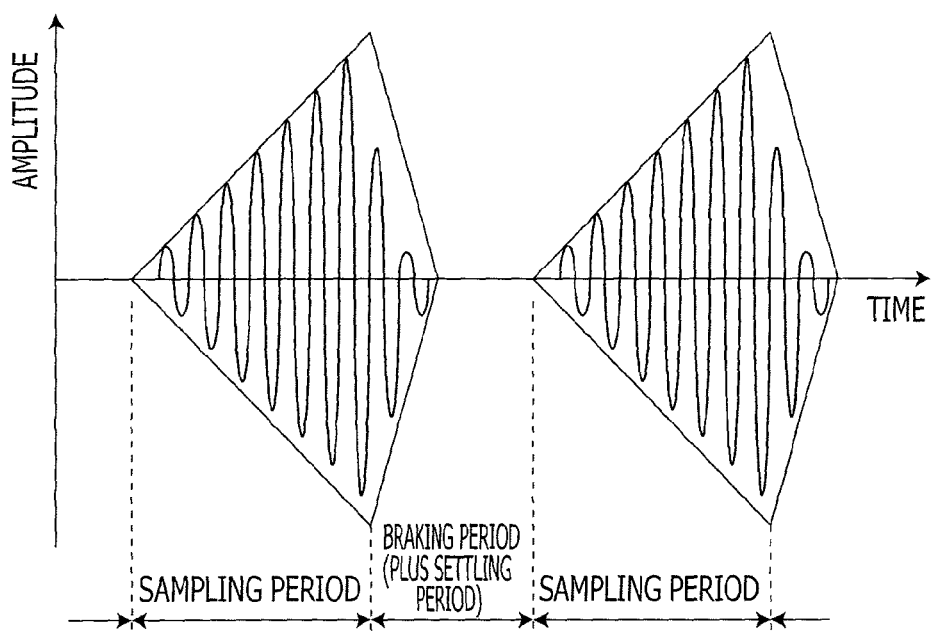
FIG. 5 A diagram to illustrate a relationship between a moving amount (amplitude) of the tip end of the optical fiber in an X (or Y) direction and sampling and braking periods (and a settling period).

The illumination light emitted from the light source 102 is emitted from the tip end 202a of the optical fiber 202 during a time period, which is from immediately after starting applying the alternating voltages until stop applying the alternating voltages to the biaxial actuators 223. In the following description, for the purpose of illustration, this time period will be referred to as the "sampling period." After elapse of the sampling period and when application of the alternating voltages to the biaxial actuator 223 is stopped, the vibration of the optical fiber 202 attenuates. The circular motion of the tip end 202a on the XY approximate plane converges along with the attenuation of the vibration of the optical fiber 202 and stops at the center axis AX after a predetermined length of time. In the following description, for the purpose of illustration, this time period, from an end of the sampling period to the time when the tip end 202a stops at the center axis AX, will be referred to as a "braking period." After elapse of the braking period, and further after standing by for a predetermined length of time, a next sampling period starts. In the following description, for the purpose of illustration, this time period, from an end of the braking period to the time when the next sampling period starts, will be referred to as a "settling period." The settling period is a waiting period for the tip end 202a to completely stop at the center axis AX. By providing the settling period, the rotation trajectory of the tip end 202a can be stabilized. By stabilizing the rotation trajectory of the tip end 202a, scanning accuracy with regard to an object can be ensured. A period corresponding to one frame is formed with one sampling period and one braking period, and the settling period may be optionally added thereto. A frame rate may be flexibly set or modified by adjusting the settling period. Thus, the settling period may be optionally set based on the relationship between a time period required for the tip end 202a to make complete stop and the frame rate. In order to shorten the braking period, a reverse-phase voltage may be applied to the biaxial actuator 223 at an initial stage of the braking period so that a braking torque may be actively applied. In FIG. 5, a relationship between a moving amount (amplitude) of the tip end 202a of the optical fiber 202 in the X (or Y) direction on the XY approximate plane and the sampling and braking periods (and the settling period) is shown.

On a frontward position of the tip end 202a of the optical fiber 202, an objective optical system 224 is disposed (FIG. 2). The objective optical system 224 is configured with a plurality of optical lenses and is held by the hollow tube 221 through lens frames, which are not shown.

The illumination light emitted from the tip end 202a of the optical fiber 202 transmits through the objective optical system 224 and forms a spot on a surface of the object. A spot formation position moves as the tip end 202a of the optical fiber 202 is driven rotatably in the spiral so that the spot scans the object two-dimensionally.

The illumination light emitted from the tip end 202a of the optical fiber 202 reflects (scatters) on the surface of the object, and a part of the reflected light enters the optical fiber 230 through one end (incident end) of the optical fiber 230. The reflected light travels through the optical fiber 230, passes through the optical connector 153, travels further through the optical fiber 112, and is detected by the photo receiver 114. The photo receiver 114 detects amounts of red-light component, green-light component, and blue-light component in the received reflection light, and pixel signals corresponding to the amounts of the received light are generated.

The pixel signals generated by the photo receiver 114 are inputted in the video signal processing circuit 116. The video signal processing circuit 116 operates under the control of the CPU 108 and generates digital pixel signals by performing sampling-and-holding and AD conversion to the pixel signals at a constant rate. In this regard, once the position (trajectory) of the tip end 202a of the optical fiber 202 during the sampling period is provided, the spot formation position in the observation area (the scanning area) corresponding to the provided position, and a signal acquisition timing (hereinafter, a "sampling point"), at which the returning light (reflected light) from the spot formation position is detected so that the digital pixel signals are obtained, are uniformly defined. Therefore, the video signal processing circuit 116 estimates the spot formation positions of the illumination light and the sampling points based on the signals to control the scan driver 210, obtains positions corresponding to the sampling points on the image (pixel positions on an endoscope image to be displayed on the monitor 300), and stores the digital pixel signals at addresses in an image memory 26 corresponding to the positions on the image. Thus, the video signal processing circuit 116 performs buffering by storing the image data formed with the spatial arrangement of point images into the image memory 118 on a frame-by-frame basis.

The buffered image data is swept out from the image memory 118 to the video signal output circuit 120 at a predetermined timing, converted into video signals complying with a predetermined standard, such as NTSC (National Television System Committee) and PAL (Phase Alternating Line), and output to the monitor 300. Thus, on a display screen of the monitor 300, an image (the endoscope image) of the object scanned by the illumination light is displayed.

As described above, in the optical scanning endoscope 200 according to the present embodiment, by feeding the drive signals from the scan driver 210 to the electrodes 223X, 223X', 223Y, 223Y' of the respective piezoelectric actuators in the biaxial actuator 223, the tip end 202a of the optical fiber 202 is driven to rotate in a spiral. Therefore, it is necessary that the scan driver 210 and the electrodes 223X, 223X', 223Y, 223Y' of the respective piezoelectric actuator are electrically connected with each other. However, an outer diameter of the biaxial actuator 223 is so notably small (e.g., 0.8 mm) that soldering the lead wires directly onto the electrodes 223X, 223X', 223Y, 223Y' of the respective piezoelectric actuator requires notably difficult operation. Therefore, in the present embodiment, this problem is solved by forming the mounting member 222 as a resin-molded component (hereinafter, "MID (Molded Interconnect Device)" component) with a surface, on which the wiring patterns can be formed.

Figure 6:
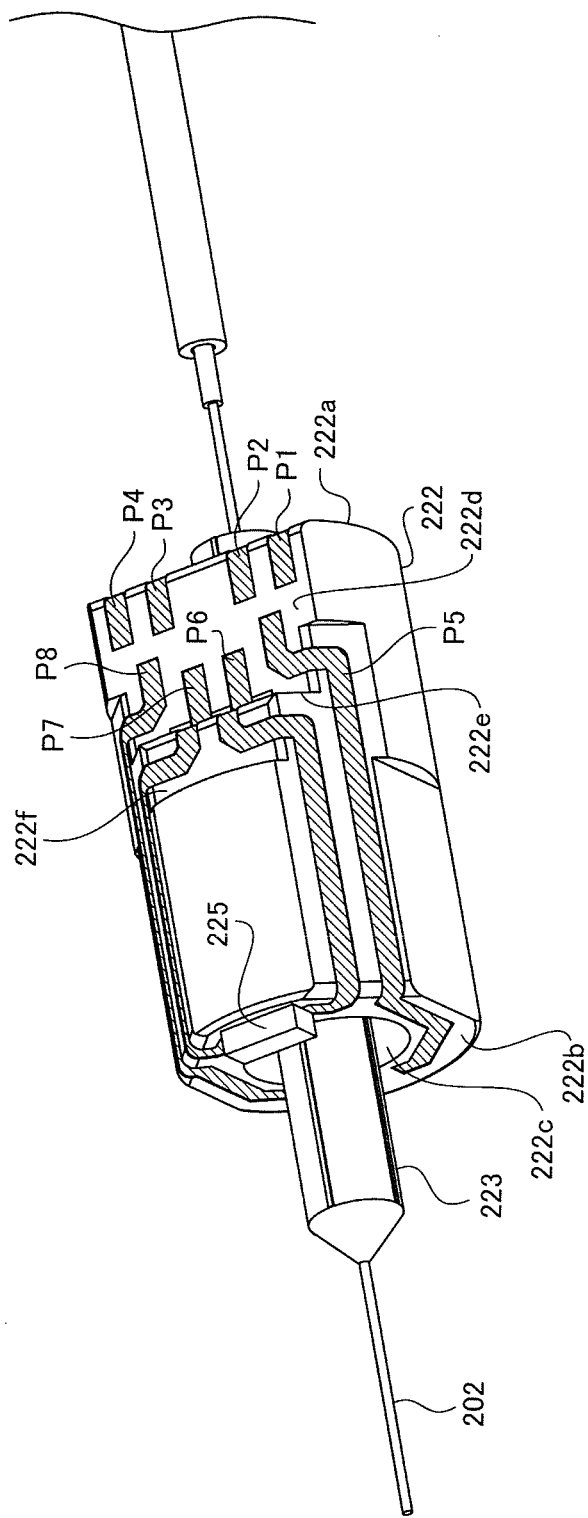
FIG. 6 A perspective view of a part including a mounting member installed in the optical scanning endoscope according to the first embodiment of the present invention.
Figure 7:
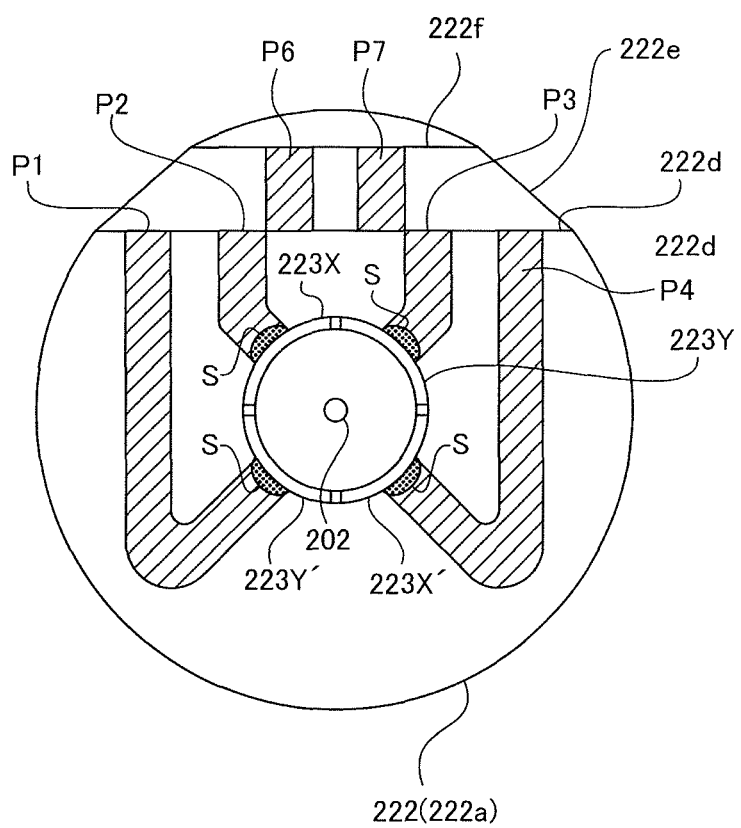
FIG. 7 A diagram to illustrate the mounting member shown in FIG. 6 viewed from a side of a proximal-end face.

FIG. 6 is a perspective view of a part including the mounting member 222 according to the present embodiment. FIG. 7 is a diagram to illustrate the mounting member 222 viewed from a side of a proximal-end face 222a (a proximal-end side of the optical fiber 202). In FIGS. 6 and 7, in order to simplify the drawings, the hollow tube 221, the objective optical system 224, and the lead wires 212 are omitted. As shown in FIGS. 6 and 7, the mounting member 222 is a substantially cylindrically-shaped MID component and is formed to have a through hole 222c, which is formed to penetrate between the proximal-end face 222a and a tip-end face 222b along a cylindrical axis thereof. While an inner diameter of the through hole 222c is slightly larger than an outer diameter of the biaxial actuator 223, by inserting the biaxial actuator 223, which is fixed to the tip end 202a of the optical fiber 202, into the through hole 222c, the biaxial actuator 223 and the optical fiber 202 are supported and fixed in the mounting member 222.

At a part of an outer periphery of the cylindrical surface on the side of the proximal-end face 222a of the mounting member 222, a first plane section 222d which is continuous from the proximal-end face 222a is formed. Meanwhile, on a side of the first plane section 222d closer to the tip-end face 222b, a step 222e which rises perpendicularly with respect to the first plane section 222d is formed. Further, on an upper side of the step 222e, a second plane section 222f which is parallel with the first plane section 222d is formed.

On a surface of the mounting member 222, the wiring patterns P1-P4 are formed. Proximal-end portions of the wiring patterns P1-P4 are arranged to be spaced apart from one another at a predetermined interval along the Y-direction (a direction orthogonal to the longitudinal direction of the optical fiber 202), on the first plane section 222d on a side of the proximal-end face 222a, and provide soldering lands. The wiring pattern P1 extends on the proximal-end face 222a from the first plane section 222d to a lower-leftward position of the through hole 222c (FIG. 7). On the other hand, a tip end portion of the wiring pattern P1 is soldered onto the electrode 223Y' for the Y-axis of the biaxial actuator 223 at a position in the vicinity of a boundary S with the through hole 222c. The wiring pattern P2 extends on the proximal-end face 222a from the first plane section 222d to an upper-leftward position of the through hole 222c (FIG. 7). On the other hand, a tip end portion of the wiring pattern P2 is soldered onto the electrode 223X for the X-axis of the biaxial actuator 223 at a position in the vicinity of a boundary S with the through hole 222c. The wiring pattern P3 extends on the proximal-end face 222a from the first plane section 222d to an upper-rightward position of the through hole 222c (FIG. 7). On the other hand, a tip end portion of the wiring pattern P3 is soldered onto the electrode 223Y for the Y-axis of the biaxial actuator 223 at a position in the vicinity of a boundary S with the through hole 222c. The wiring pattern P4 extends on the proximal-end face 222a from the first plane section 222d to a lower-rightward position of the through hole 222c (FIG. 7). On the other hand, a tip end portion of the wiring pattern P4 is soldered onto the electrode 223X' for the X-axis of the biaxial actuator 223 at a position in the vicinity of a boundary S with the through hole 222c. Thus, the electrodes 223X, 223X', 223Y, 223Y' of the biaxial actuator 223 are electrically connected with the wiring patterns P1-P4 respectively on the proximal-end face 222a of the mounting member 222 and drawn onto the first plane section 222d.

Meanwhile, on a surface of the mounting member 222, wiring patterns P5-P8 to mount functional components are formed, and proximal-end portions of the wiring patterns P5-P8 are arranged on a side of the tip-end face 222b on the first plane section 222d. The wiring pattern P6 extends from the first plane section 222d through the step 222e, the second plane section 222f, and the outer periphery of the cylindrical surface of the mounting member 222, to an upper side of the tip-end face 222b (FIG. 6). The wiring pattern P7 extends from the first plane section 222d through the step 222e, the second plane section 222f, and the outer periphery of the cylindrical surface of the mounting member 222, to an upper side of the tip-end face 222b (FIG. 6). A tip end portion of the wiring pattern P6 and a tip end portion of the wiring pattern P7 are arranged to be spaced apart from each other at a predetermined interval to face each other on the tip-end face 222b of the mounting member 222, and terminals of the thermistor 225 are soldered thereonto respectively. In other words, the terminals of the thermistor 225 are drawn onto the first plane section 222d via the wiring patterns P6, P7. The wiring patterns P5, P8 extend from the first plane section 222d through the outer periphery of the cylindrical surface of the mounting member 222 to a lower side of the tip end surface 222b (FIG. 6). A tip end portion of the wiring pattern P5 and a tip end portion of the wiring pattern P8 are arranged to be spaced apart from each other at a predetermined interval to face each other on the tip-end face 222b and are configured to be soldered with terminals of a functional component such as a thermistor. In the present embodiment, the wiring pattern P5 and the wiring pattern P8 are reserved patterns, by which a functional component would be installed, but no functional component is installed in between these patterns. Thus, the terminals of the functional components to be mounted on the mounting member 222 can be electrically connected at the tip end portions of the wiring patterns P5-P8, drawn onto the first plane section 222d, and arranged to be spaced apart from one another at the predetermined interval along the Y-direction. In this regard, the proximal-end portions of the wiring patterns P5-P8 provide soldering lands on the first plane section 222d.

Figure 8:
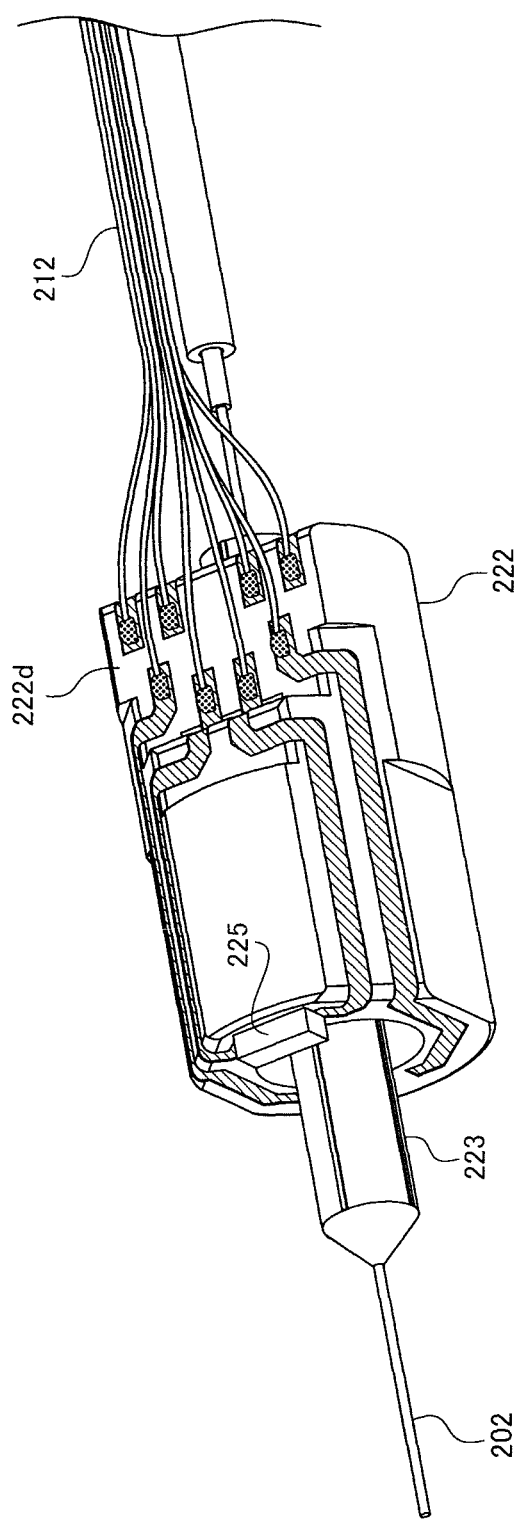
FIG. 8 A diagram to illustrate a state, in which lead wires are connected with the mounting member shown in FIG. 6.

As described above, the wiring patterns P1-P8 according to the present embodiment formed on the mounting member 222 draw the electrodes 223X, 223X', 223Y, 223Y' of the respective piezoelectric actuators in the biaxial actuator 223 and the terminals of the functional component (the thermistor 225) mounted on the mounting member 222 onto the first plane section 222d. Therefore, by soldering the electrodes 223X, 223X', 223Y, 223Y' of the respective piezoelectric actuators and the lead wires 212, which feed the necessary signals (and power) to the functional components, onto the soldering lands formed on the first plane section 222d, the electrodes 223X, 223X', 223Y, 223Y' of the respective piezoelectric actuators in the biaxial actuator 223 and the scan driver 210 are electrically connected with one another, and the terminals of the functional component mounted on the mounting member 222 can be electrically connected to the sub-CPU 206. Thus, according to the present embodiment, unlike the conventional configuration, it is not necessary to solder the lead wires directly onto the electrodes 223X, 223X', 223Y, 223Y' of the respective piezoelectric actuators, which are arranged at each 90 degrees on the outer periphery of the cylindrical surface of the biaxial actuator 223. Rather, soldering can only be taken place on the first plane 222d; therefore, operability is significantly improved. In this regard, according to the present embodiment, as shown in FIG. 6, the tip end portions of the wiring patterns P1-P4 and the tip end portions of the wiring patterns P5-P8 disposed on the first plane section 222d are arranged not to face one another so that, when the lead wires 212 are soldered on the first plane section 222d, the adjoining lead wires 212 should not interfere with one another. FIG. 8 is a diagram to illustrate a state, in which the lead wires 212 are soldered with the wiring patterns P1-P8. As shown in FIG. 8, according to the configuration of the present embodiment, the lead wires 212 can be soldered at the secured positions (i.e., at the soldering lands formed on the first plane section 222d); therefore, it may not be necessary to take extra lengths for the lead wires 212 into consideration. Accordingly, the lead wires 212 may not necessarily be curved, as they have been conventionally, and may be arranged along the longitudinal direction of the optical fiber 202 without being forced; therefore, the diameter of the tip end portion of the optical fiber 202 may be even more effectively downsized without causing a wasteful space around the tip end portion of the optical fiber 202.

Figure 9A:
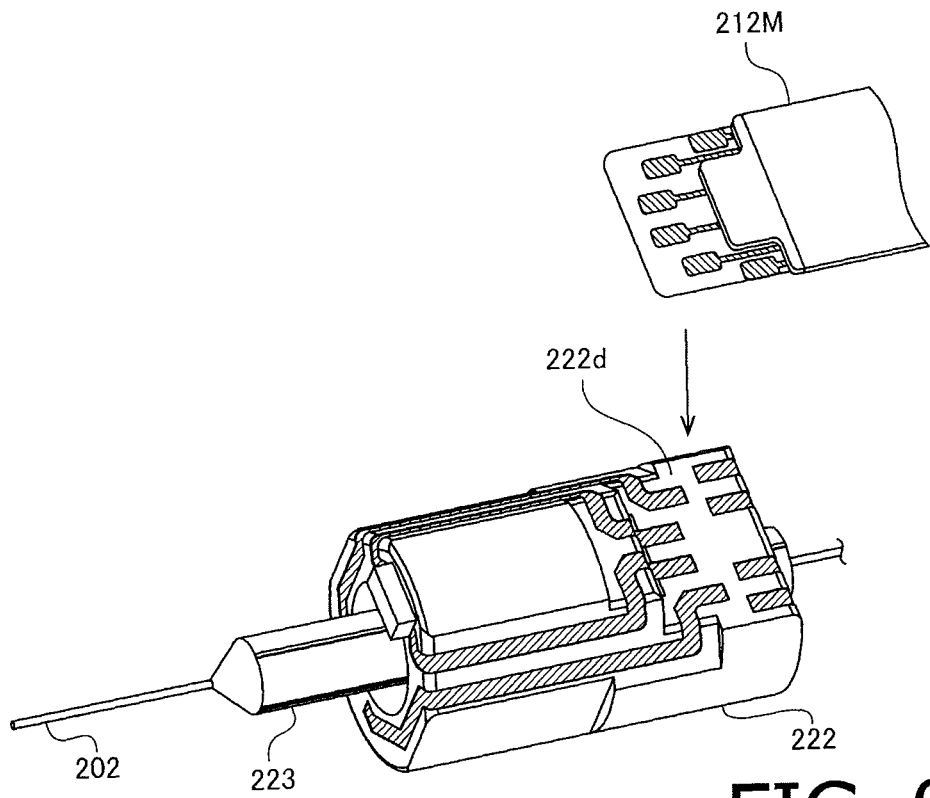
FIG. 9 A perspective view of a part including a mounting member installed in the optical scanning endoscope according to a modified example of the first embodiment of the present invention.
Figure 9B:
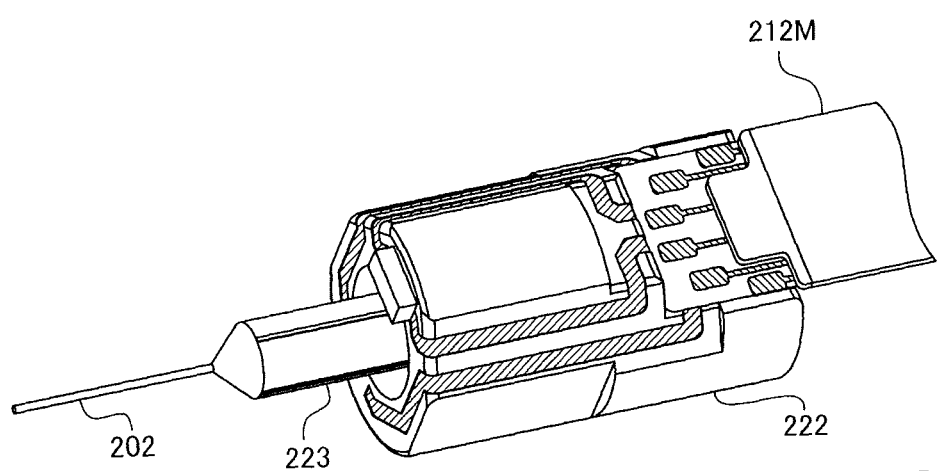

The foregoing is the explanation of the embodiment of the present invention; however, the invention is not limited to the above described embodiment, but can be modified in various ways within the scope of the technical concept of the invention. For example, in the above described embodiment, the scan driver 210 and the sub-CPU 206 are connected with the wiring patterns P1-P8 formed on the mounting member 222 by the lead wires 212. However, for example, the connection may be established by a flexible board in place of the lead wires 212. FIG. 9 is a diagram to illustrate a configuration, in which the scan driver 210 and the sub-CPU 206 are connected with the wiring patterns P1-P8 formed on the mounting member 222 by a flexible board 212M. As shown in FIG. 9A, at a tip end portion of the flexible board 212M, a land pattern corresponding to the wiring patterns P1-P8 (i.e., the soldering lands) on the first plane section 222d is formed. After applying soldering paste on the wiring patterns P1-P8 on the first plane section 222d, and placing a tip end portion of the flexible board 212M on the first plane section 222d (FIG. 9B), by processing through in a reflow furnace, the soldering may be accomplished. According to this configuration, it is effective in an aspect that the soldering operation can be automated.

Figure 10:
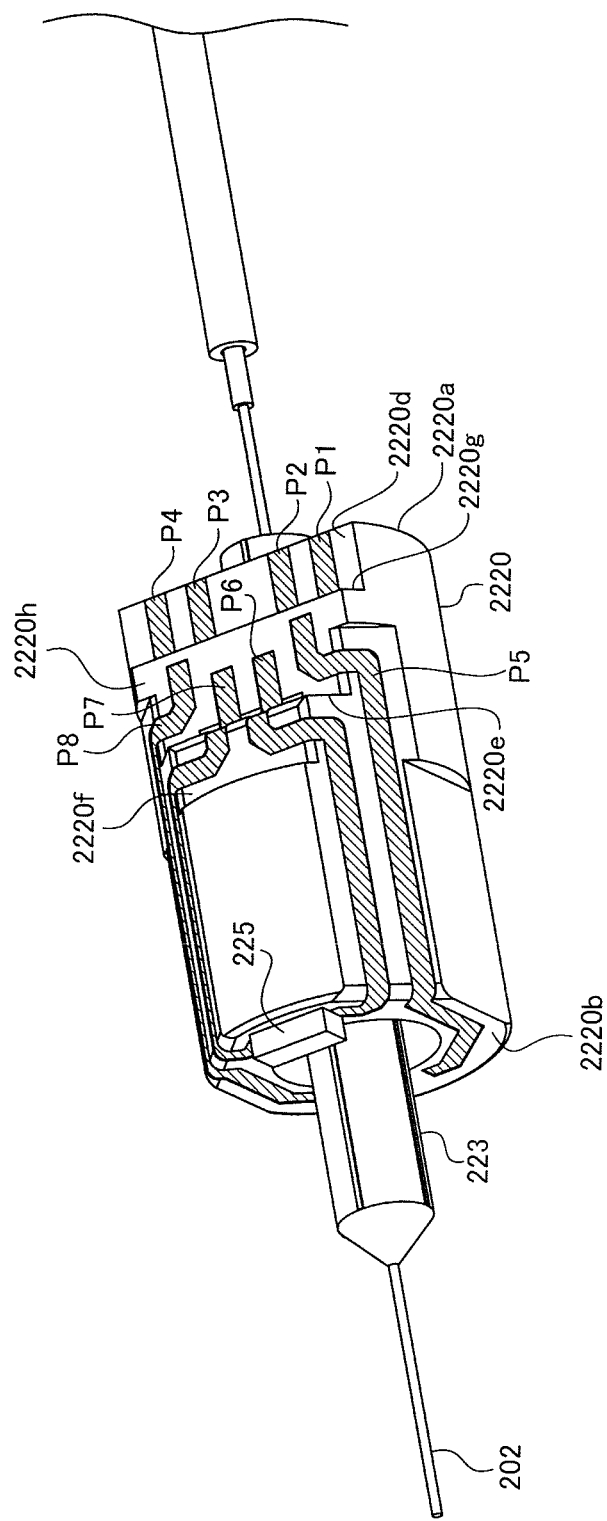
FIG. 10 A perspective view of a part including a mounting member installed in the optical scanning endoscope according to a second embodiment of the present invention.
Figure 11:
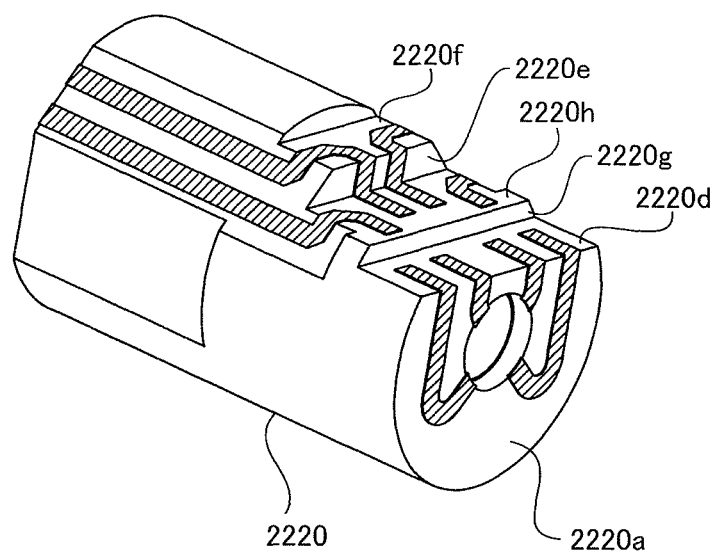
FIG. 11 A perspective view to illustrate the mounting member shown in FIG. 10 viewed from a side of the proximal-end face.
Figure 12:
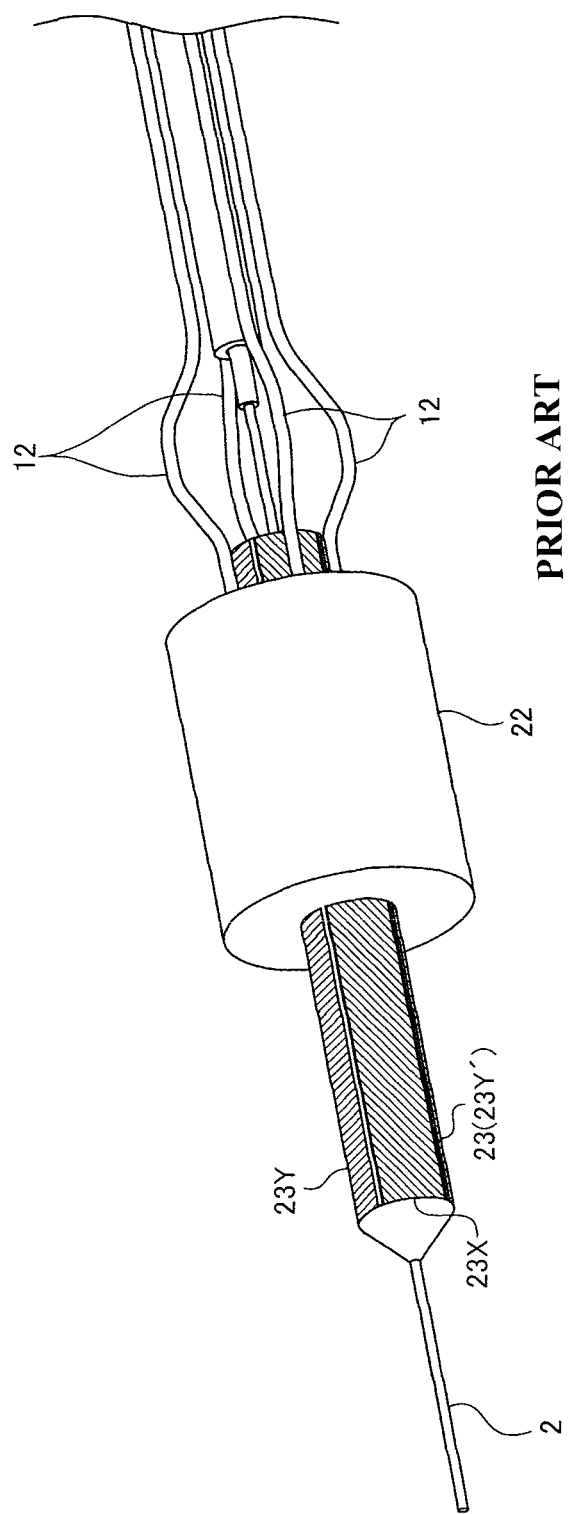
FIG. 12 A diagram to illustrate the configuration of the tip end of the optical fiber in the conventional optical scanning endoscope.

FIG. 10 is a perspective view of a part including a mounting member 2220 installed in an optical scanning endoscope according to a second embodiment of the present invention. FIG. 11 is a diagram to illustrate the mounting member 2220 viewed from a side of a proximal-end face 2220a. The mounting member 2220 according to the present embodiment is different from the mounting member 222 in the first embodiment in respects that a step 2220g and a third plane section 2220h are formed in between a first plane section 2220d and a second plane section 2220f, that the proximal-end portions of the wiring patterns P1-P4 are formed on the first plane section 2220d, and that the proximal-end portions of the wiring patterns P5-P8 are formed on the third plane section 2220h. In other words, in the present embodiment, arrangement of the lead wires 212 is divided into two steps, which are the first plane section 2220d and the third plane section 2220h; therefore, interference among the adjoining lead wires 212 is reduced, and the soldering operation can become even easier. Further, while in the first embodiment, the tip end portions of the wiring patterns P1-P4 and the tip end portions of the wiring patterns P5-P8 are arranged not to face one another so that the interference between the adjoining lead wires 212 can be avoided, in the present embodiment, it is not necessary to take the interference between the adjoining lead wires 212 into consideration. Therefore, the proximal-end portions of the wiring patterns P1-P4 and the proximal-end portions of the wiring patterns P5-P8 may be formed at equal interval on the first plane section 2220d and the third plane section 2220h respectively. According to this configuration, amounts of clearance between the soldering lands can be widened in comparison with the first embodiment, and the soldering operation can become even easier. In this regard, according to the present embodiment, the arrangement of the lead wires 212 is divided into the two steps of the first plane section 2220d and the third plane section 2220h; however, the division may not necessarily be limited to two steps, but the arrangement may be divided into more (a plurality of) plane sections, which are formed to be lower in steps from the tip-end face 2220b toward the proximal-end face 2220a. In this configuration, while the wiring, patterns P1-P4 are arranged on the side of the proximal-end face 2220a of the mounting member 2220, and while the wiring patterns P5-P8 are arranged on the side of the tip-end face 2220b of the mounting member 2220, it may be efficient in arrangement that the proximal-end portions of the wiring patterns P1-P4 are arranged on a plane section which is closest to the proximal-end face 2220a of the mounting member 2220, and the proximal-end portions of the wiring patterns P5-P8 are arranged on a plane section different from the proximal-end portions of the wiring patterns P1-P4 (i.e., a plane section closer to the tip-end face 2220b). For another example, the proximal-end portions of the wiring patterns P1-P4 and the proximal-end portions of the wiring patterns P5-P8 may not necessarily be arranged on the same plane sections respectively. For example, the proximal-end portions of the wiring patterns P1-P4 may be distributed to be arranged on different plane sections.

What is claimed is:

1. An optical scanning endo scope, comprising:
    an optical fiber configured to guide light entering from an incident end thereof to an emitting end thereof and to emit the light from the emitting end;
    a fiber driver arranged in vicinity of the emitting end of the optical fiber and comprising a plurality of actuators, the plurality of actuators being configured to bend the optical fiber by pressing lateral sides of the optical fiber in directions orthogonal to a longitudinal direction of the optical fiber;
    a mounting member comprising a substantially cylindrical molded interconnect device with a surface, on which a plurality of wiring patterns are provided, the mounting member supporting the fiber driver along a cylinder axis;
    a control circuit configured to transmit driving signals to each of the plurality of actuators and to control an amount of bending and a direction of bending of the optical fiber; and
    a wiring member configured to electrically connect the plurality of wiring patterns of the mounting member with the control circuit,
    wherein the mounting member comprises a plane section an outer periphery of a cylindrical surface of the mounting member on a proximal-end face side of the mounting member;
    wherein the plurality of wiring patterns are arranged such that end portions thereof on one side are positioned on the plane section to provide a plurality of soldering lands thereat, the plurality of wiring patterns including at least a plurality of first patterns, each end portion of which on the other side is electrically connected with one of the plurality of actuators respectively on the proximal-end face of the mounting member; and
    wherein the wiring member is connected to the plurality of soldering lands.

2. The optical scanning endoscope according to claim 1, wherein each of the plurality of soldering lands is arranged on the plane section spaced from each other at a predetermined interval along a direction orthogonal to the longitudinal direction of the optical fiber.

3. The optical scanning endoscope according to claim 1, wherein the plurality of wiring patterns include a plurality of second patterns, end portions of which on the other side are connected to a functional component on a tip-end face of the mounting member.

4. The optical scanning endoscope according to claim 3, wherein the soldering lands of the plurality of first patterns are arranged on a proximal-end face side of the plane section; and
    wherein the soldering lands of the plurality of second patterns are arranged on a tip-end face side of the plane section.

5. The optical scanning endo scope according to claim 4, wherein the soldering lands of the plurality of first patterns and the soldering lands of the plurality of second patterns are arranged not to face one another on the plane section.

6. The optical scanning endo scope according to claim 3, wherein the plane section comprises a plurality of stepwise planes which are provided to have lower heights from the tip-end face side toward the proximal-end side;
    wherein the soldering lands of the plurality of first patterns are arranged on one of the plurality of stepwise planes which is closest to the proximal-end face; and
    wherein the soldering lands of the plurality of second wiring patterns are arranged on a different one of the plurality of stepwise planes from the one of the plurality of step wise planes on which the soldering lands of the first wiring patterns are arranged.

7. The optical scanning endoscope according to claim 3, wherein the functional component is a thermistor.

8. The optical scanning endoscope according to claim 1, wherein the wiring member is lead wires.

9. The optical scanning endoscope according to claim 1 wherein the wiring member is a flexible board.

10. The optical scanning endoscope according to claim 2, wherein the plurality of wiring patterns include a plurality of second patterns, end portions of which on the other side are connected to a functional component on a tip-end face of the mounting member.

11. The optical scanning endoscope according to claim 4, wherein the plane section comprises a plurality of stepwise planes which are provided to have lower heights from the tip-end face side toward the proximal-end side;
    wherein the soldering lands of the plurality of first patterns are arranged on one of the plurality of stepwise planes which is closest to the proximal-end face; and
    wherein the soldering lands of the plurality of second wiring patterns are arranged on a different one of the plurality of stepwise planes from the one of the plurality of step wise planes on which the soldering lands of the first wiring patterns are arranged.

12. The optical scanning endoscope according to claim 5, wherein the plane section comprises a plurality of stepwise planes which are provided to have lower heights from the tip-end face side toward the proximal-end side;
    wherein the soldering lands of the plurality of first patterns are arranged on one of the plurality of stepwise planes which is closest to the proximal-end face; and
    wherein the soldering lands of the plurality of second wiring patterns are arranged on a different one of the plurality of stepwise planes from the one of the plurality of step wise planes on which the soldering lands of the first wiring patterns are arranged.

* * * * *